United States Patent
Noe et al.

(10) Patent No.: US 6,853,927 B2
(45) Date of Patent: Feb. 8, 2005

(54) METHOD OF AND APPARATUS FOR MEASURING PLANARITY OF STRIP, ESPECIALLY METAL STRIP

(75) Inventors: Andreas Noe, Kerken (DE); Rolf Noe, Mühlheim (DE)

(73) Assignee: WG Bergwerk- Und Walzwerk-Maschinenbau GmbH, Duisburg (DE)

( * ) Notice: Subject to any disclaimer, the term of this patent is extended or adjusted under 35 U.S.C. 154(b) by 14 days.

(21) Appl. No.: 10/417,808

(22) Filed: Apr. 17, 2003

(65) Prior Publication Data
US 2003/0236637 A1 Dec. 25, 2003

(30) Foreign Application Priority Data
Jun. 4, 2002 (DE) .......................................... 102 24 938

(51) Int. Cl.$^7$ ................................................. G01L 1/00
(52) U.S. Cl. .............................. 702/41; 73/37.5; 72/6.1
(58) Field of Search ...................... 702/41, 42; 73/37.5; 72/8.7, 9.1, 12.3, 11.4, 6.2, 7.1, 7.6, 8.1, 6.1; 700/152

(56) References Cited

U.S. PATENT DOCUMENTS

| | | | | |
|---|---|---|---|---|
| 4,261,190 A | * | 4/1981 | Fapiano | 72/8.7 |
| 4,269,051 A | * | 5/1981 | Clarke et al. | 72/8.7 |
| 4,289,005 A | * | 9/1981 | Cabaret et al. | 72/8.7 |
| 4,485,497 A | * | 12/1984 | Miura | 700/152 |
| 4,674,310 A | * | 6/1987 | Ginzburg | 72/11.4 |
| 5,235,835 A | * | 8/1993 | Sakai et al. | 72/9.1 |
| 5,379,631 A | * | 1/1995 | Kira et al. | 73/37.5 |
| 6,164,104 A | * | 12/2000 | Noe et al. | 72/12.3 |
| 6,668,626 B2 | * | 12/2003 | Grefve et al. | 73/104 |

* cited by examiner

Primary Examiner—John Barlow
Assistant Examiner—Hien Vo
(74) Attorney, Agent, or Firm—Herbert Dubno

(57) ABSTRACT

A method of measuring planarity of strip in a strip-rolling line or a strip-processing line in which a measuring beam, a plurality of measuring beams or discrete measuring pins in an inclined pattern across a measuring roller, measures the tension forces acting upon the strip to form a force summation foundation across the strip width. A tension distribution function is derived from the force summation function by taking derivatives of the force-summation function with respect to the width dimension of the strip and, if desired, dividing that derivative by the thickness of the strip.

10 Claims, 11 Drawing Sheets

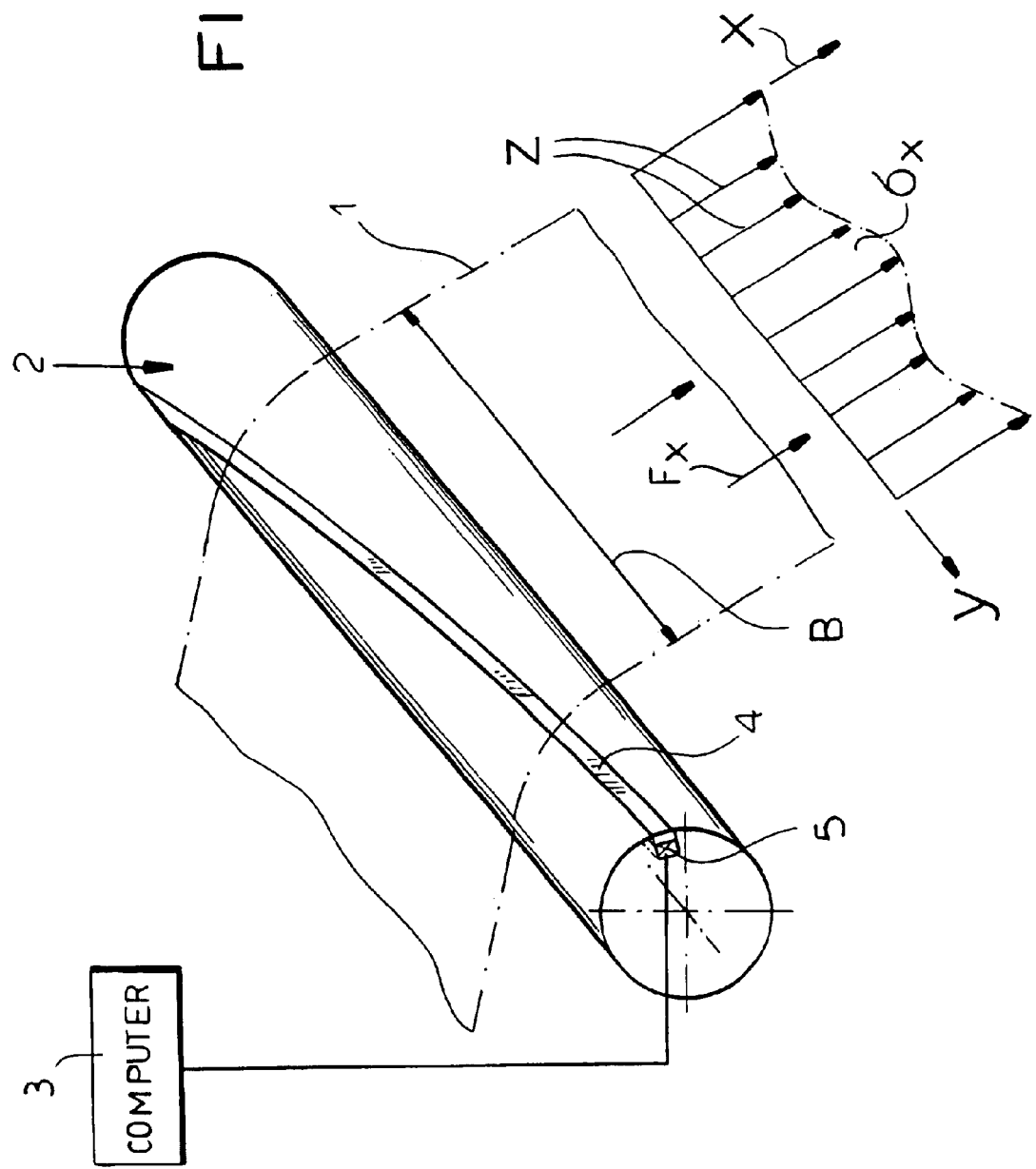

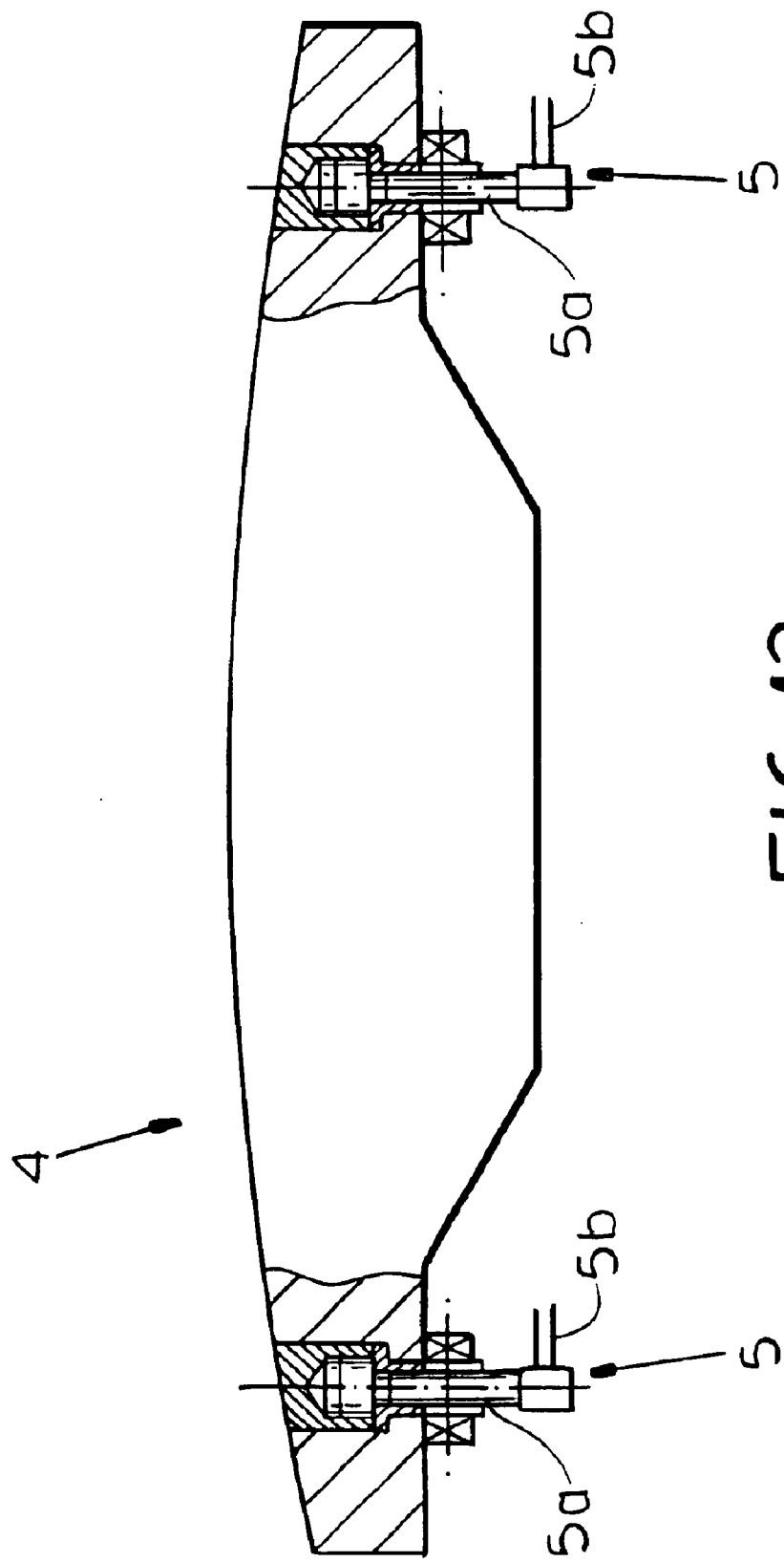

METHOD OF AND APPARATUS FOR MEASURING PLANARITY OF STRIP, ESPECIALLY METAL STRIP

FIELD OF THE INVENTION

Our present invention relates to a method of and to an apparatus or device for measuring the planarity of strip, especially metal strip, passing through a strip-rolling line or a strip-processing line. More particularly, the invention relates to the measurement of strip planarity in a system in which tension forces acting on the strip are determined at least sectionwise across the width of the strip and are evaluated.

BACKGROUND OF THE INVENTION

Metal strip after the strip-forming process, e.g. rolling, may have defects with respect to planarity of the strip which can be length differences with respect to longitudinal zones of the strip across the width thereof. The defects generally are detectable as planarity defects and it is customary to subject the strip to leveling depending upon the deviation of the strip from true planarity. Indeed, deviation from planarity may arise not only in strip-rolling lines but also in strip-processing lines and the lack of planarity can be a function of the deformation by rolling, of various leveling methods and annealing or heat treatment generally of the strip.

Especially in the cold rolling of strip, it can be observed that there is a certain tendency toward corrugation of the strip which can arise because of differences in strip thickness across the strip or longitudinally therealong and as a consequence of the different degrees of plastic deformation which can be carried out on the strip or can arise from the cold rolling process. Apart from deviations in planarity there may be distortion in the strip itself which are evident as strip camber or edge waviness.

As a consequence, it has been customary to carry out planarity measurements in metal strip traversing a strip-rolling line or a processing line. For example, the tension force in the strip can be determined and divided by the strip width and strip thickness and utilized to provide a feedback signal which is used to control strip tension. Corrugations in the strip have created problems where the strip was to be used in some industries, for example in the automobile sector, especially when the lack of planarity of the strip exceeded certain limits. As a measure of deviation from planarity, a so-called I-unit (IU) has been developed. An IU corresponds to a tension difference of $10^{-5}$ across a strip or across a longitudinal segment of the strip. For example, when the tension differences across the strip are measured in length differences, for example $\Delta l/l$ is less than $10^{-5}$, the lack of planarity is deemed to be less than 1 IU. In this relationship $\Delta l$ is, of course, the difference in length as measured cross the strip while l is the length over which that difference is applicable.

Any producer of strip must as a rule determine the planarity limits of the product and thus planarity measurements must be taken and these measurements utilized within the rolling line or strip processing line to control the rolling or strip processing line or to identify the quality of the strip produced. Where such measurements are taken, they can be used in real time to regulate a shaping or processing process, i.e. in parallel therewith.

EP 1 116 952 A2 describes a contactless method of measuring planarity while a system utilizing measurement rollers in contact with a continually traveling strip to determine the tension therein is described for example DE 199 18 699 A1.

While the contactless measurement process mainly utilizes acoustic waves, ultrasonic waves or electromagnetic measurements to detect the planarity, the roller approach provides a magnetic measurement system and has the greatest use in practice. The measurement roll approach of DE 199 18 699 A1 utilizes a multiplicity of measurement pickups which can be received in recesses and spaced from the wall of the measurement roller. The measurement roller can then be subdivided into so-called disk segments which have been described for example in EP 1 182 424 A1. With the aid of the sensors, radial force measurements are made where the strip is looped around a roller and the output signals are measurements of the local tension which can be divided by the width of the segment and the strip thickness.

The planarity defects resulting from length differences correspond to varying tensions at the respective segments since the latter are measurements of the extent of elongation in the metal strip and the effect thereof on the planarity. Reference may be to the work "Formabweichungen in B ändern: Einteilung, Entstehung, Messung und Beseitigung sowie quantitative Bewertungsmethoden" (Shape Deviations in Strip: Classification, Creation, Measurement and Evidence as well as Quantitative Evaluation Methods by Gert Mücke, Kai F. Karhausen and Paul-Dieter Pütz (Stahl and Eisen 122 (2002) No. 2, Pages 33 ff).

The known mechanical measurement methods have some basic drawbacks in that only a limited number of measurement points are obtained over the strip width with local tension measurement techniques. That means that a sufficiently precise resolution requires a large number of sensors and hence a comparatively costly measurement roller and thus significant expense in evaluating the results. Furthermore, measurements at edges of the strip are especially problematical because it is there possible that a sensor will only partially cover the strip edge or be looped by the strip. The result can be errors. Errors can also be produced when the position of the strip edge is measured.

OBJECTS OF THE INVENTION

It is the principal object of the present invention to provide an improved method of measuring the planarity of strip and especially metal strip passing through a strip-rolling line for a processing line whereby the disadvantages or drawbacks enumerated above can be obviated.

More specifically, it is an object of the invention to provide a planarity measurement method for such strip which will enable the tension distribution across the strip to be measured with a high degree of precision, fine resolution and comparatively inexpensively and so that errors in such measurements in the region of the strip edges are avoided.

Another object is to provide a device which is especially suitable for carrying out the method.

SUMMARY OF THE INVENTION

These objects are attained, in accordance with the invention in a method of measuring planarity of strip passing through a strip-rolling line or strip-processing line with the steps of:

(a) measuring tension forces ($F_x$) acting upon the strip at least sectionwise over a width of the strip;

(b) summing the measured tension forces ($F_x$) to form a force-summation function (F(y)) across the strip width; and (c) deriving a tension distribution function ($\sigma_x(y)$) from the force-summation function ($F(y)$).

The device for measuring such planarity can comprise:

an elongated sensor unit having at least one sensor for measuring tension forces ($F_x$) acting upon the strip at least sectionwise over a width of the strip, the sensor unit being oriented at an inclination to a direction of travel of the strip; and a computer unit connected to the sensor unit for summing the measured tension forces ($F_x$) to form a force-summation function ($F(y)$) across the strip width and deriving a tension distribution function ($\sigma_x(y)$) from the force-summation function ($F(y)$).

According to the invention, therefore, tension forces are exclusively measured across the width of the strip and optionally summed and the resulting summation force function over the strip width is subjected to a differentiation to produce a continuous tension distribution function. If desired, this tension distribution function can be divided by the thickness of the strip to obtain a specific tension distribution function ($\sigma_x(y)=dF(y)/dy/s$ in which the first term is the tension distribution function and the second term is the first derivative of the force summation function $F(y)$ divided by the thickness s. As a rule, the respective tension forces are added, although this is not absolutely necessary. If the addition does not yield a summation function, the summation function referred to can be a summation force function defined only by the course of the respective measured tension force across the width of the strip from which the tension distribution function can be derived.

According to a feature of the invention, therefore, the tension distribution function ($\sigma_x(y)$) is derived from the force-summation function ($F(y)$) as the first derivative ($\sigma_x(y)=dF(y)/dy$)) thereof. The tension forces, or if one wishes infinitesimal partial tension forces, are measured in the individual longitudinal zones of the strip successively starting from one strip edge or continuously across the strip width to the other strip edge to integrate or sum that force. The detection of the tension force can be contactless as by the use of sensors which are acoustic, ultrasonic or electromagnetic, or via sensors which come into contact with the strip, in every case providing tension force outputs across the strip.

The sensor or sensors thus measure the tension forces over the strip width with corresponding time offset and enable the summation of the tension forces from strip edge to strip edge and along a predetermined measurement line or across a predetermined measurement surface to yield the force-summation function.

During the planarity measurement between a starting point and an ending point of the measurement or a starting region and ending region of the sensor with respect to its cross section, the measurement takes place over a measuring roller within a certain measurement angle which itself is within the looping angle of the strip and the measurement roller. Stated otherwise, the starting and ending points or starting and ending regions of the measurement line or of the sensor in projection on the cross section of the measurement roll is within the looping angle of the strip, e.g. the metal strip around the measurement roller.

The starting and ending points or starting and ending regions of the measurement line or of the sensor in projection on the cross section of the measurement roll is within the looping angle of the strip, e.g. the metal strip around the measurement roller.

The measurement range over which the sensor or sensors is or are effective for the edge to edge measurement, can be subdivided into a plurality of partial measurements whose individual measured tension forces can be combined to produce the force summation function. The latter can be formed in, for example, a computer unit provided for this purpose.

It is thus possible to subdivide the strip width into respective longitudinal zones in which respective partial tension force measurements are made and from which respective force summation functions are obtained or from which an overall force summation function for each scan of the strip width by the sensor set is generated.

According to a feature of the invention, the device comprises at least one measurement roller around which the strip is at least partially looped to form a looping angle ($\alpha$) of the strip on the roller, the elongated sensor unit being a measurement beam integrated in the roller.

The strip can be scanned with the measurement beam between a starting position along one edge of the strip and an ending position along an opposite edge of the strip over a measurement angle on the roller within the looping angle ($\alpha$).

In this case, a single sensor member is provided which carries out a measurement over the full strip width for each rotation of the measurement beam and, where a plurality of measurement beams are provided in angularly spaced relationship, a number of such scans from edge to edge can be provided with each revolution of the measurement roller. Where the sensor is subdivided to provide axially offset sensors on the roller, successive longitudinal zones of the strip are scanned. Where the measurement beam in vertical projection lies at an angle of inclination to the main axis of the measurement roller, a time offset of the measurement from edge to edge is compensated by having one portion of the sensor leading and another trailing in the direction of rotation.

Since the sensor member progressively comes within the looping angle, for an exactly planar strip, there is a linear increase in the tension force across the strip width. This is not the case for a nonplanar strip.

The measured total force falls after reaching a plateau or maximum (when the sensor in the form of a measurement beam completely captures the tension force). The advancing band rotation of the measurement roll then passes out of the looping angle. Ideally there are rising and falling flanks with different slopes.

The tension distribution function is therefore derived by taking the derivative of the force summation function across the strip width. This allows deviation of the force summation function from linearity to be readily detected. When the derivative of the force summation function across the strip width is further divided by the strip thickness, one obtains a specific tension force distribution of the strip as a function of the strip width.

The measurement process of the invention can be carried out in an ideal case with a single sensor and this need not have the multiple sensors of the prior art and can be free from the drawbacks described which arise because of sensors which measure the tension force along the edges of the strip and thus at the ends of the measurement range.

The precision of the measurement is then dependent upon the resolution of the sensor. In the simplest case a force measurement member, for example, a strain gauge or force measuring cell (load cell) can respond to the force applied to the measurement beam. Where desirable, two such force measuring members can be provided in spaced relationship along the beam for measuring the force applied thereto by the strip.

However, the resolution can be increased by subdividing the force measurement so that it is done with a plurality of such beams which can be offset from one another across the strip width so that each individual measurement beam or partial beam can measure the force applied by a respective longitudinal zone of the strip. The partial beams each cover a respective partial region of the measurement roll.

For example, if three partial measurement beams are provided, the maximum force which is applied to each partial measurement beam is one-third of the total force applied by the strip to the measurement roll and representing the tension on that strip as it is looped around the measurement roll. The measurement precision can thereby be increased by a factor of three.

The resolution of the force detection can also be increased by making each measurement beam small and by inclining the measurement beam so that the length of the measurement beam can be greater than the width of the longitudinal zone of the strip which the particular partial beam measures. A sliding mean value is obtained from the partial beam and from the sliding mean value the tension distribution function is derived again by taking the first derivative of it.

The partial measurement beam integrated in the measurement roll can have a low mass, especially when it is comparatively small so that measurement errors resulting from centrifugal force on the measurement beam as a result of rotation of the measurement roll can be zero or negligible.

The method and the apparatus for practicing the method provide planarity measurement for strips, especially metal strip, utilizing a simple structure which gives the force summation function and the tension distribution derived therefrom in a simple manner.

BRIEF DESCRIPTION OF THE DRAWING

The above and other objects, features, and advantages will become more readily apparent from the following description, reference being made to the accompanying drawing in which:

FIG. 1a is a perspective view showing a system according to the invention;

FIG. 10b is a side view of the measurement roller and measurement beam of FIG. 10a;

FIG. 12 is a side view of a measurement beam for integration in a measurement roller and showing two force-measuring sensors in the form of strain gauges or load cells.

SPECIFIC DESCRIPTION

A strip 1 which, according to the invention can be a metal strip and is understood to be traveling continuously in a strip processing line (e.g. a pickling, dressing, annealing, tempering, descaling or coating line) or in a forming line such as a rolling mill line, has its planarity measured across its width B by passing the strip over a roller 2, hereinafter referred to as a measurement roller, so that the strip is looped partly around the roller, i.e. contacts the roller at an upstream location and leaves the roller at a downstream location and between the upstream and downstream locations is in contact with the roller over a certain arc length which corresponds to a looping angle.

The measurement roller 2 has a length at least equal to the strip length B and is provided with at least one sensor, for example, the sensor bar 4 which can extend over the length L of the measurement roll, where L is greater than or equal to B.

Figure 1B:
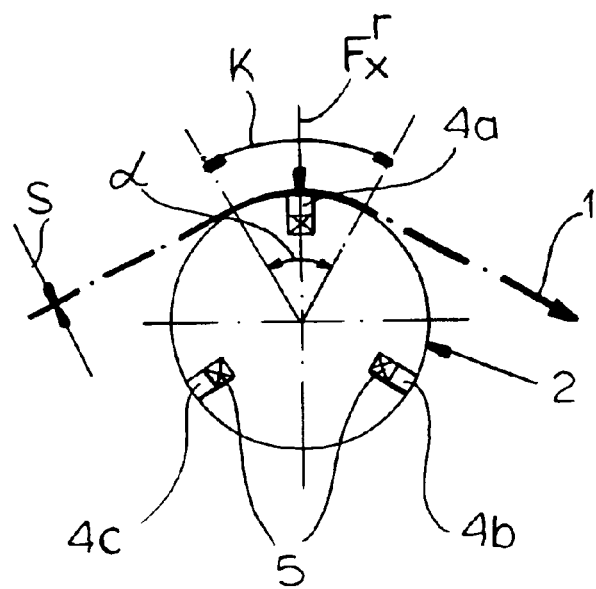
FIG. 1b is a cross sectional view through the measurement roller and illustrating the measurement beams angularly spaced therein.

FIG. 1a shows that the sensor bar 4 and the load cells 5 on which that bar bears, can extend at an inclination to the axis of the roller 2 while FIG. 1b shows that the looping angle α extends over a fraction of the measurement roller 2. FIG. 1b also indicates that a plurality of such measurement bars can be provided at 4a, 4b and 4c in angularly equispaced relationship.

Figure 2:
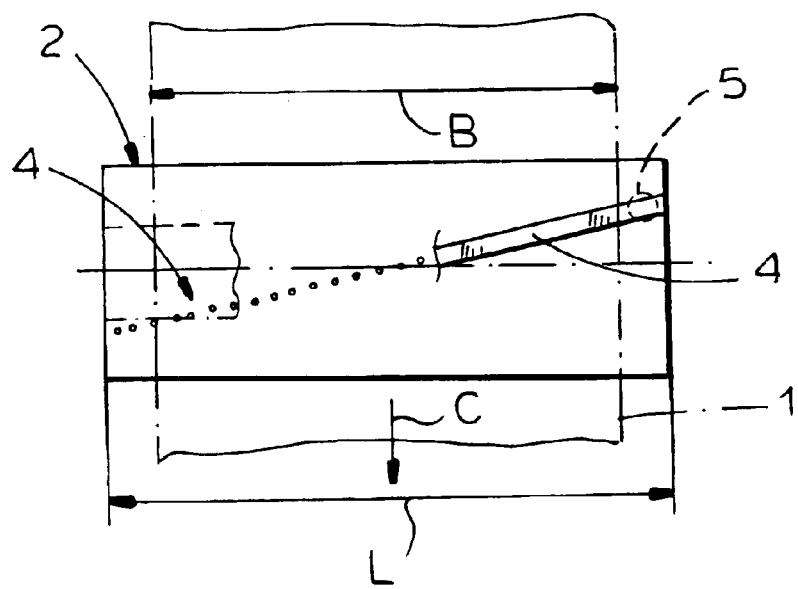
FIG. 2 is a schematic elevational view, partly broken away, of the device of FIG. 1a limited to the most important components.

FIG. 2 shows the relationship between the length L and the strip width B and by means of the arrow C indicates the travel of the strip in the x direction. The dimensions of the length L and the width B are in the y direction where x and y are Cartesian coordinates in the plane of the strip 1. The system of the invention responds to the tension force $F_x$ on the strip and the summation of the tension forces $F_x$ and the calculation of the distribution function $\sigma_x$ are shown by a computer unit 3 shown in FIG. 1a. The computer 3, of course, is connected to the sensor 4, 5 for the tension force $F_x$.

The beam 4, which extends helically over a partial turn in the measurement roller 2, is radially displaceable on that roller and bears at its ends on two load cells or strain gauges 5 (see FIGS. 1a and 12) to produce the electrical signals which are processed in the computer 3.

In spite of the measurement beam 4, an array of pins can be provided which can be radially shiftable in respective bores and which output electrical signals representing force measurements by engagement with the strip as described in DE 199 18 699 A1 mentioned previously. Each of these pins can directly bear on a force-measuring unit such as a load cell, outputting its signal to the computer unit 3. Alternatively, the pins can act upon an internal tube functioning as a measuring beam to transmit pressure to a load cell 5 outputting the force measurement signal.

The measurement roller 2 in any of the embodiments described enables a planarity of the strip 1 to be detected. It is assumed that during the measurement, the tension applied to the strip around the measurement roller 2 is sufficient so that all of the infinitesimal strip zones across the width B are practically rigid and thus that any corrugations or camber in the strip have been stretched out. In that case, all of the length differences Δl between the individual zones across the width of the strip and represented by the vector arrows Z can be given in terms of elongation differences in the strip travel direction x as:

$$\Delta \varepsilon_x = \frac{\Delta l}{l}$$

The result is a tension reference in the x direction as given by:

$$\Delta \sigma_x = \frac{\Delta l}{l} \cdot E = \frac{\Delta F_x}{B \cdot s},$$

where E is the modulus of elasticity of the strip material, $F_x$ is the tension force in the x direction, B is the strip width and s, the strip thickness.

From this latter relationship it is clear that changes in the tension $\Delta \sigma_x$ can be derived from the measurement of the tension force $F_x$ (when one divides the tension force $F_x$ by the strip width B and the strip thickness s). This force $F_x$ or changes in this force $\Delta F_x$ are determined with the measurement roll 2. The corresponding tension force $F_x$ in the strip travel direction x need not be directly measured but rather can be obtained in terms of a radial component $F^r_x$ resulting from the looping of the strip 1 around the measurement roll 2 (compare FIG. 1b).

Figure 3:
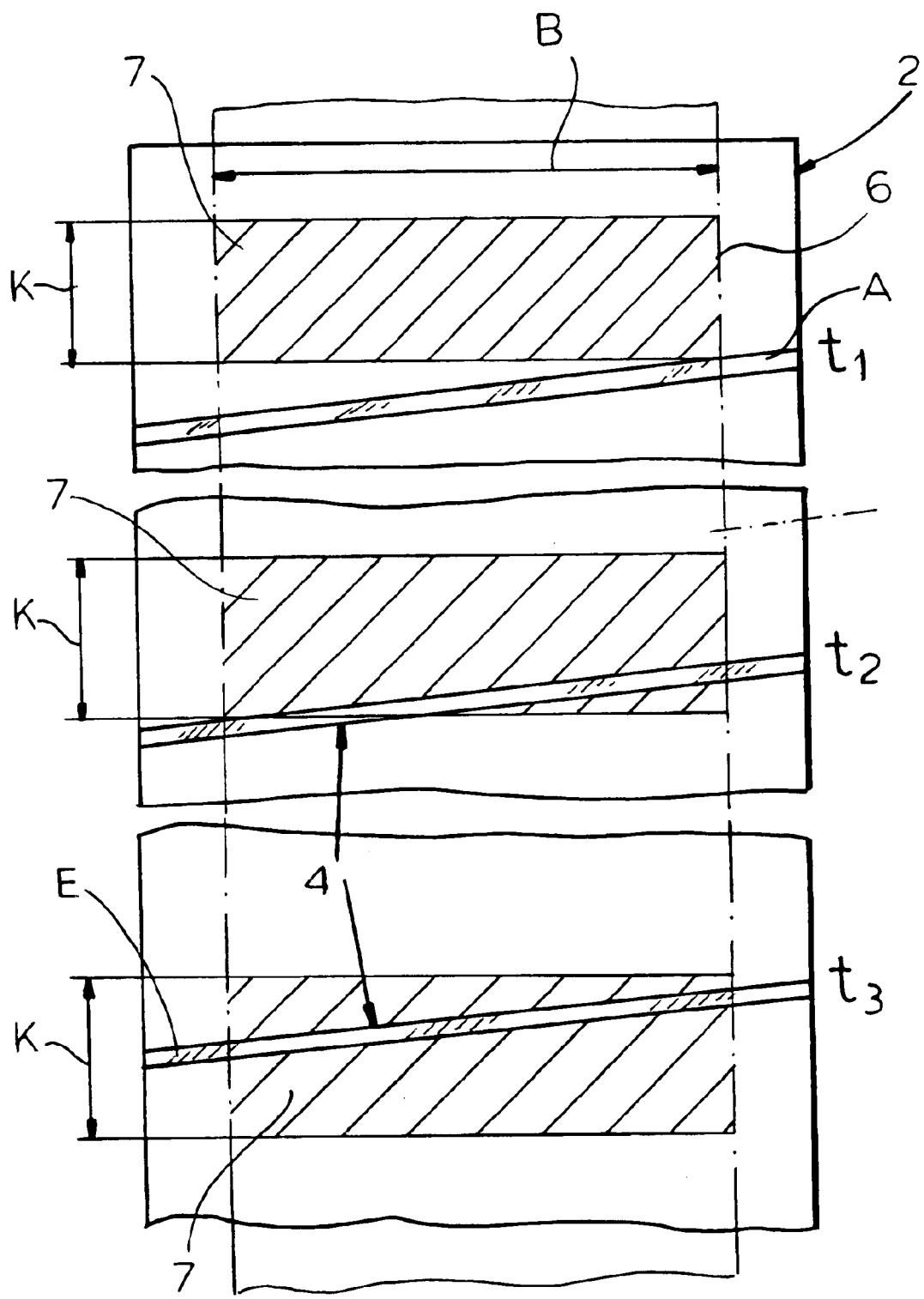
FIG. 3 is a diagram showing a metal strip at different points during and prior to a measurement process.

From FIGS. 2 and 3 it will be apparent that the sensor 4, 5 or the measurement roll 2 can be inclined with respect to the strip travel direction x and in this manner by comparison to the state of the art measurements in, for example, DE 199 18 699 A1, the tension force $F_x$ is not detected sectionwise over the strip width B or y, but rather is continuously obtained by what amounts to a scanning across the width of the strip.

For this purpose the measurement roll obtains tension force $F_x$ at time-spaced intervals as has been shown diagrammatically in FIG. 3, initially at time $t_1$, subsequently at time $t_2$ and then at time $t_3$ at successive angular positions of the measurement roll 2 corresponding to the simultaneous travel of the strip 1 continuously around the measurement roll.

The time $t_1$ represents the starting point and starting region A of the measurement and the beginning of the contact length K with which the beam 4 lies in measurement contact with the strip. This contact length K is defined by a contact area 7 whose magnitude is given by K×B (compare FIG. 3) corresponding to the area in which there is a contact between the beam 4 and the strip 1. The looping angle α (compare FIG. 1b) corresponds to the contact length K.

As soon as the starting point or starting region of the measurement beam 4 reaches the edge 6 of the strip, the force measuring cells 5 register a signal representing the radial component $F^r_x$ of the tension force Fx which is detected by the measuring beam 4. As the strip 1 continues to travel in the direction x and the strip rolls along the measuring roller 2, the measuring beam 4 engages the strip in its inclined orientation successively across the entire contact area or measurement area represented by hatching at 7 in FIG. 3.

Figure 4:
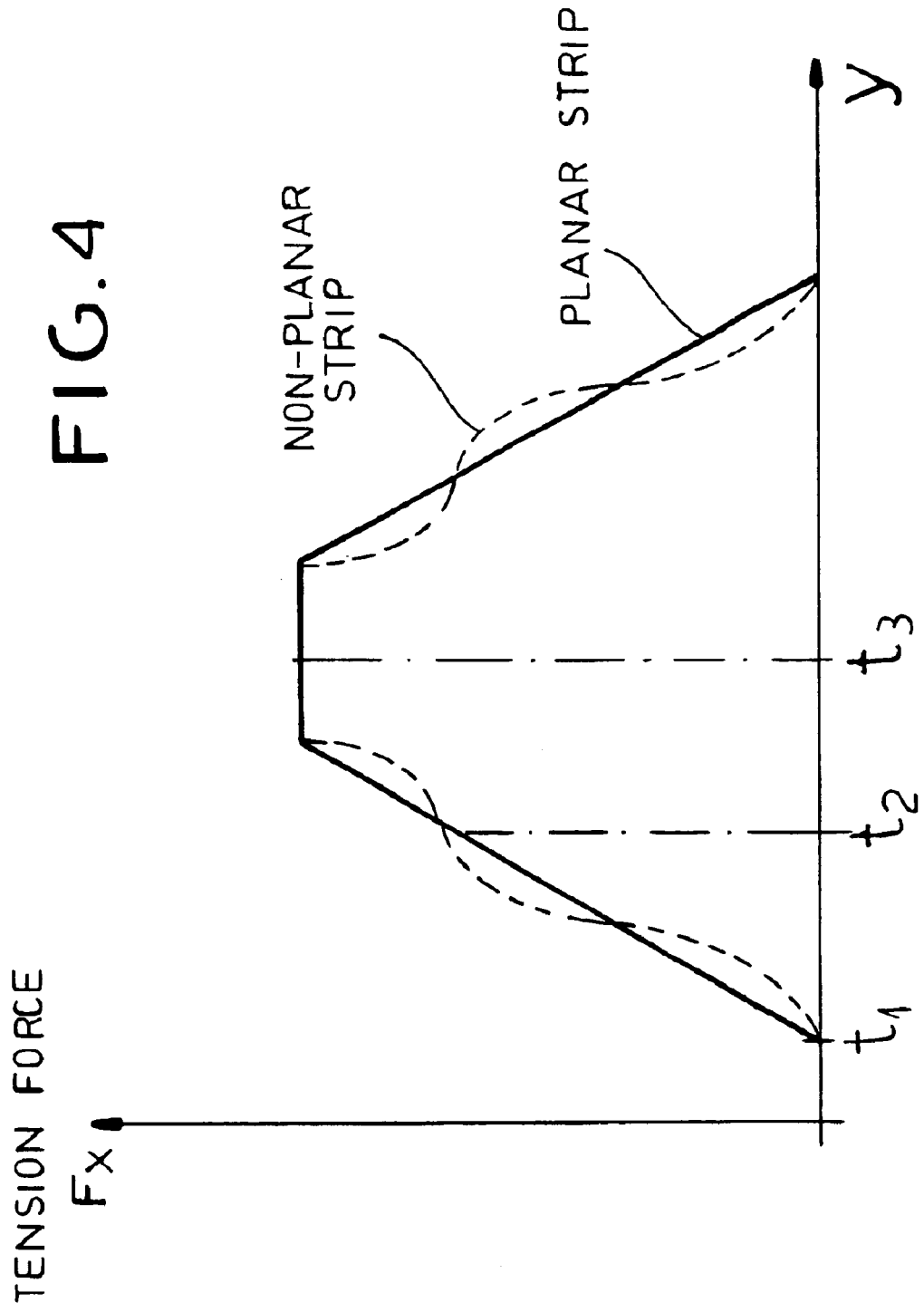
FIG. 4 is a graph of the measurement described in connection with FIG. 3 and representing the tension force $F_x$ across the strip width B in terms of the distance y along the strip width direction showing values at successive times $t_1$, $t_2$, $t_3$.

At the point $t_2$, for example, the measurement is made further into the contact area or region 7 and thus the force measured by the load cell increases (see FIG. 4). The force measurement continues to the end point or end region E of the measurement beam 5 at which the measurement beam is no longer in contact with the strip.

As shown in FIG. 4, the measured tension force Fx will have a rising flank, a descending flank and a maximum in the form of an plateau in which the measurement beam 4 lies fully within the contact region 7.

When the strip is precisely planar, the tension force Fx detected by the measurement beam will linearly increase, assuming that there are no elongation differences across the width of the strip and the coefficient Δl/l will have a zero value. There is no ΔFx in the tension force Fx. When, however, the strip is corrugated or possesses a degree of waviness or camber resulting from differential elongation, this is recognized as fluctuations in the tension force Fx as measured and has been shown in broken lines in FIG. 4 for the nonplanar strip.

Figure 5:
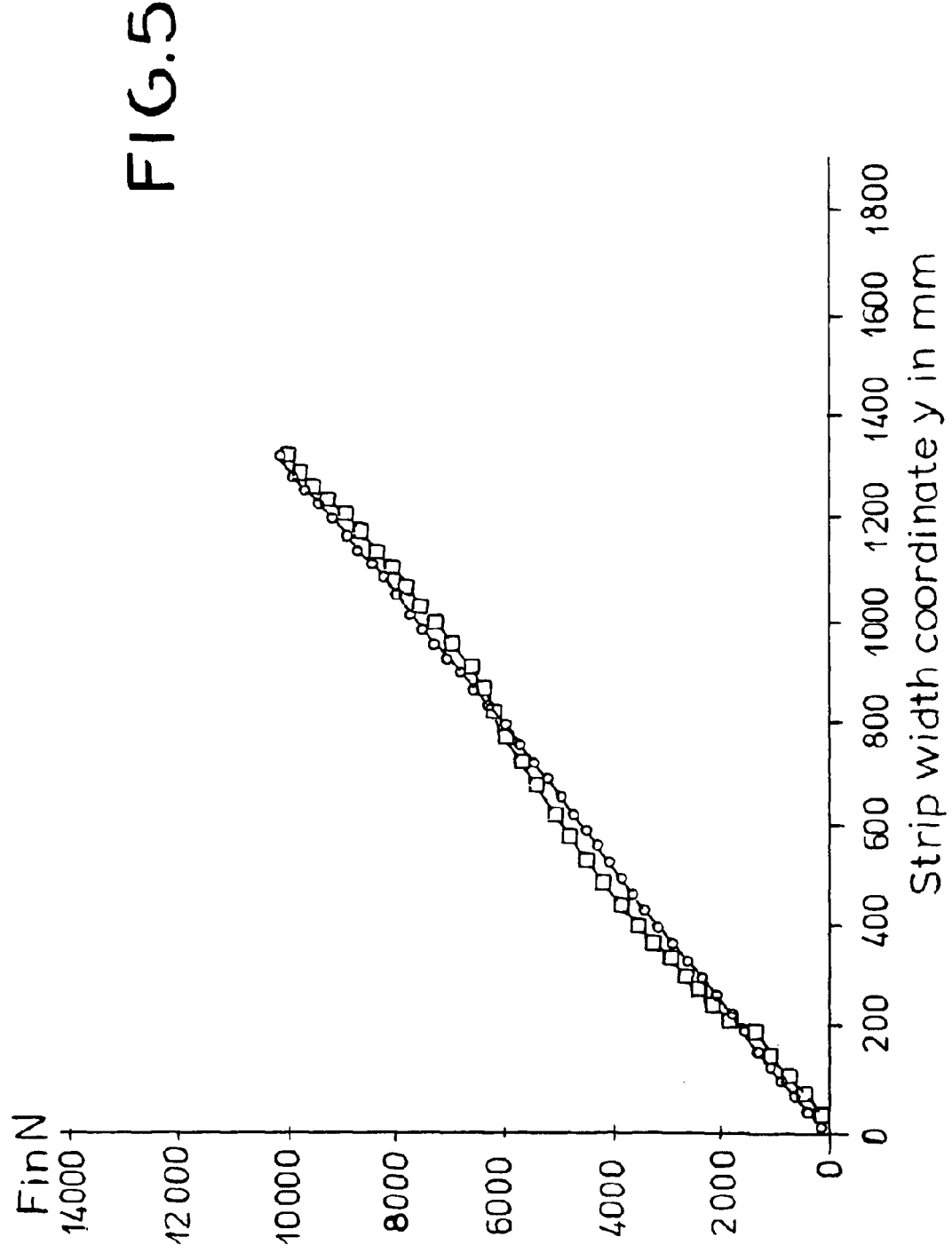
FIG. 5 is a graph of the force summation function F(y) for a planar strip and for a corrugated strip.

This difference can also be seen in FIG. 5 in which the tension force applied to the strip in newtons N as plotted against the strip width coordinate y in mm. Here the measurements for a planar strip (points or circles) are compared with the measurements for a corrugated strip (squares). The ordinate represents the force summation function, i.e. F=ΣFx over the strip width at the particular strip width coordinate y.

Figure 6:
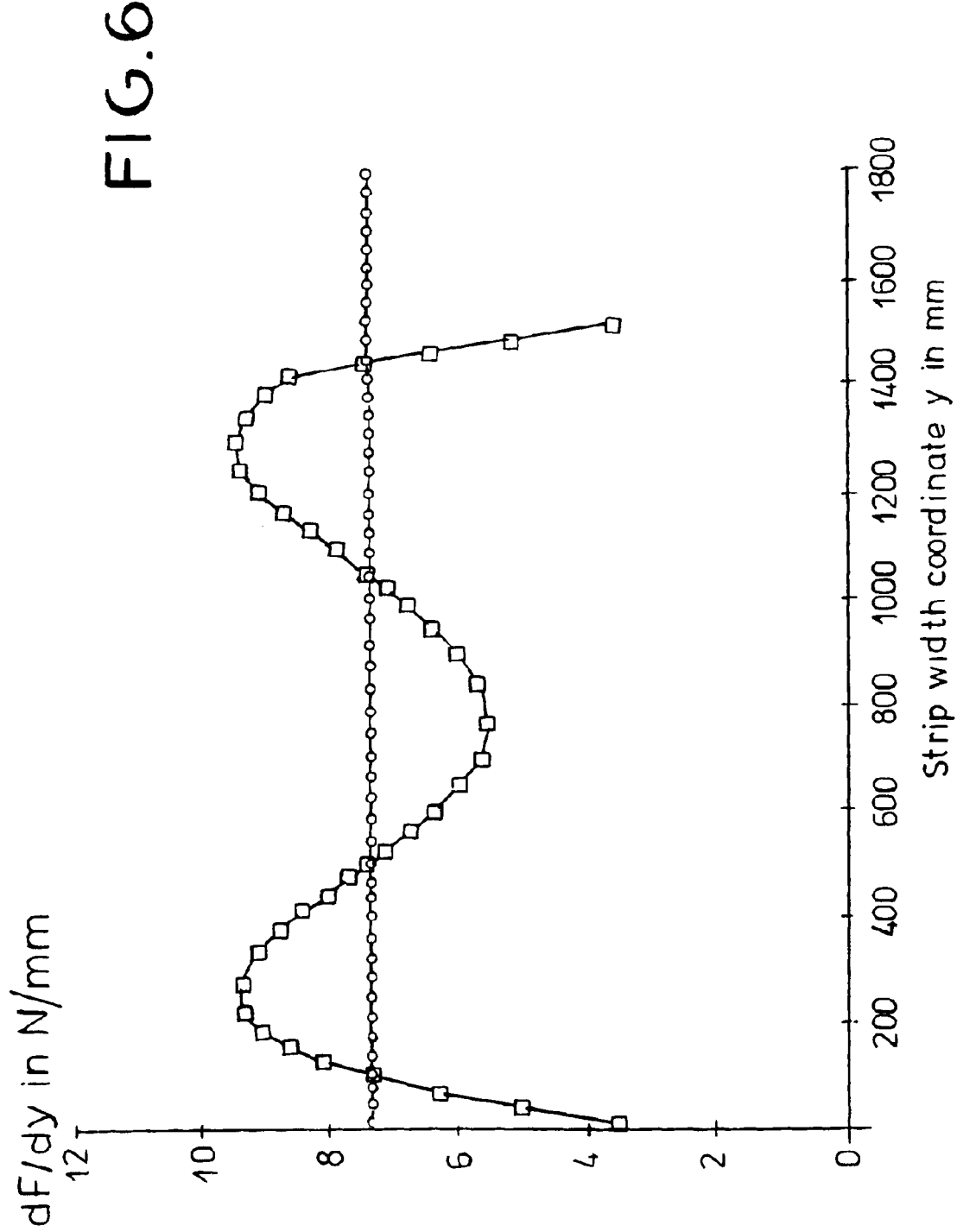
FIG. 6 is a graph of the first derivative of the tension force F/dy where F is the force summation function, across the strip width y.

If one then takes the first derivative of the force summation function F(y) with respect to the strip width coordinate y, i.e. forms the differential dF/dy, one obtains the tension force distribution across the strip width as plotted in FIG. 6.

FIG. 6 plots the differential dF/dy in N/mm versus the strip width coordinate y in mm. The squares represent the measurements for a strip having corrugations, i.e. differential elongated parts while the circles or points represent the results for a planar strip.

Figure 7:
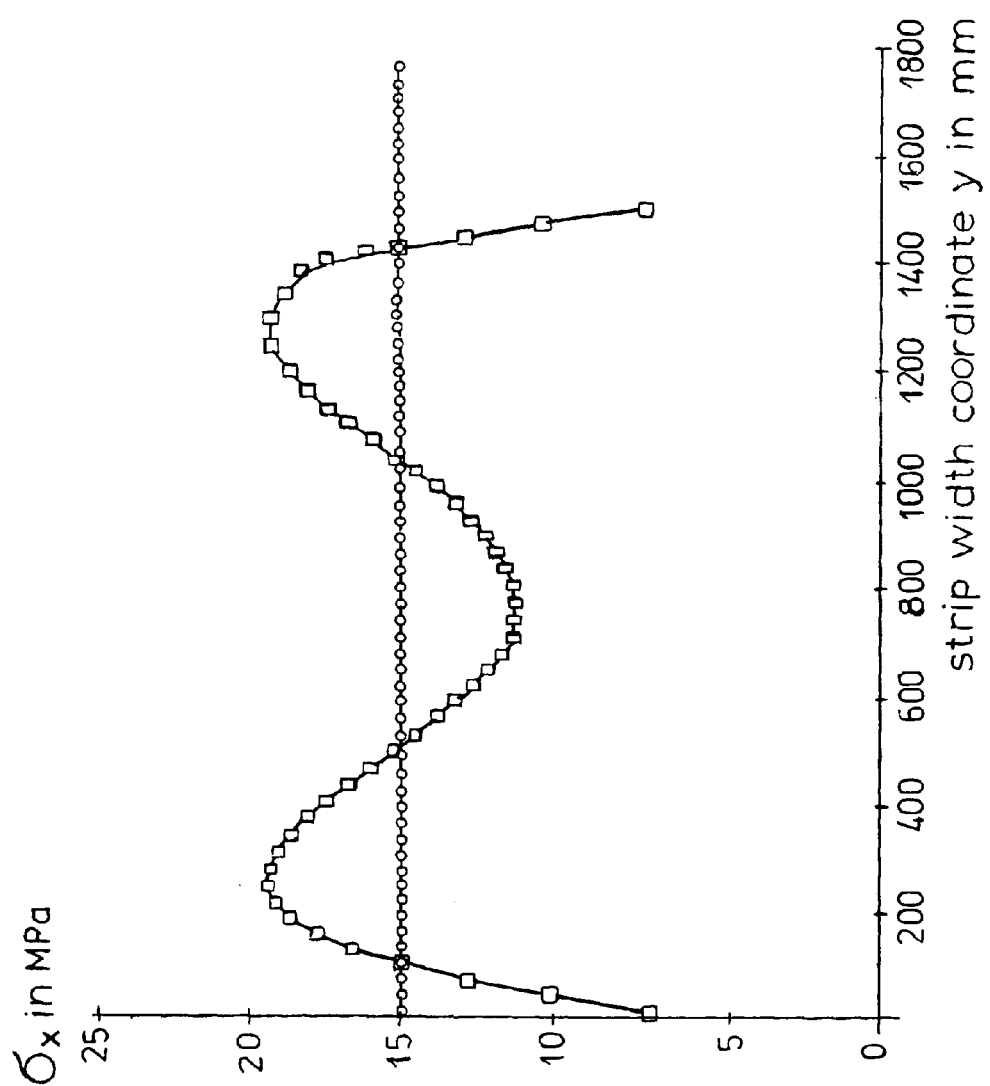
FIG. 7 is a graph of the tension distribution function $\sigma_x(y)$ as given by the graph of FIG. 6.

In the case of the specific differential coefficient, i.e. the differential coefficient dF/dy divided by the strip thickness s, one obtains directly a specific tension distribution function, $\sigma_x(y)$ across the strip width and illustrated in FIG. 7 in which the tension distribution function is plotted along the ordinate in megaPascal MPa versus the strip width coordinate y in mm.

FIGS. 6 and 7 correspond to the measurement only along a fraction of the total measurement represented by FIG. 4, namely, the rising flank ahead of the plateau. A similar result could be expected for the descending flank.

Figure 8:
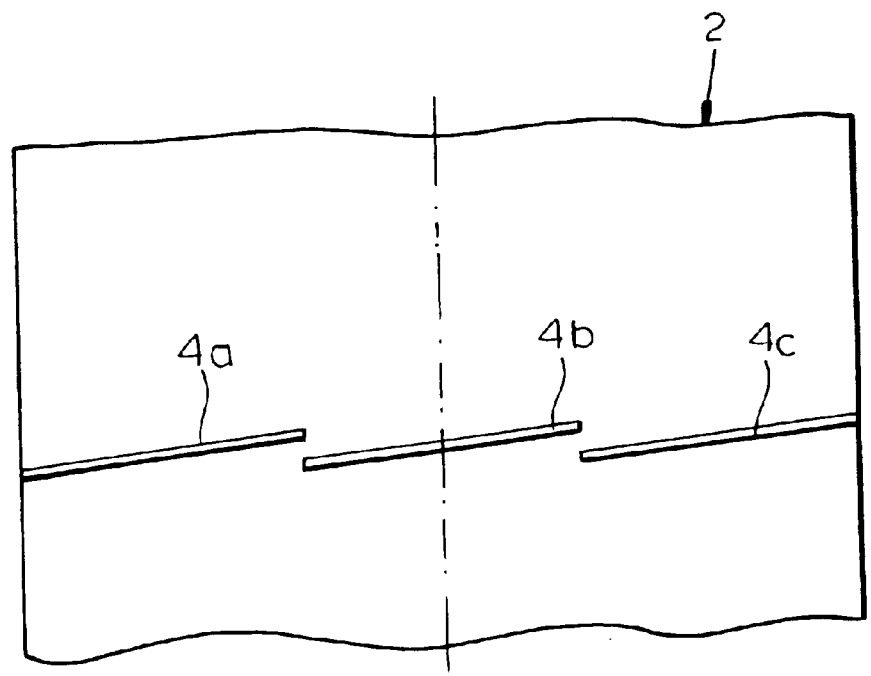
FIGS. 8 and 9 are diagrams showing other configurations of the measurement roller.

FIG. 8 shows that the measurement beam can be subdivided into a plurality of partial measurement beams 4a, 4b, 4c which can correspond to three longitudinal measurement zones along the strip and the number of such zones can be increased if desired. Each of the measurement beams 4a, 4b, 4c then need only take up one-third of the total tension force and as a result the measurement precision or resolution can be significantly increased.

FIG. 1b shows the only diagrammatically further option where the measurement roller has the three measurement beams angularly spaced around the periphery of the measurement roller 2 and each beam is provided with a plurality of measurement cells 5 so that for each revolution of the roller 2, there will be a number of measurement zones as shown in FIG. 3. That too enables an increase in the measurement precision.

Figure 9:
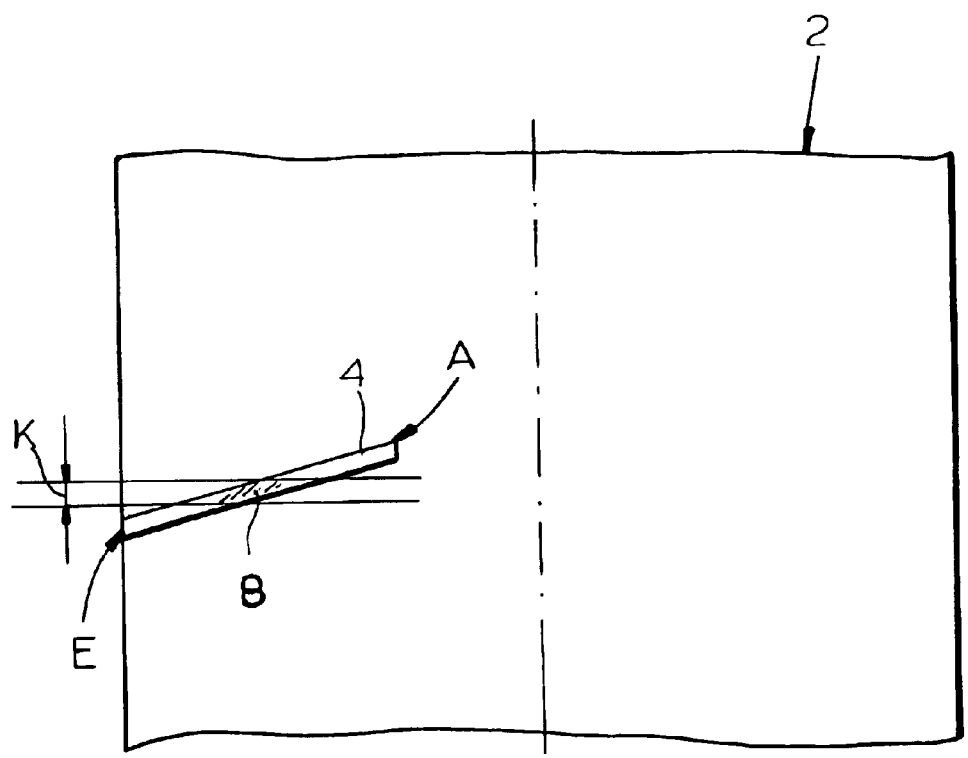

FIG. 9 shows that the measurement beams 4 can be made so small and inclined at such an angle that the starting or end edge regions will occupy only a limited contact length K and hence only a limited arc of the measurement roller 2 during the starting and final stages of the measurement. Because the contact region 8 of the starting or finishing edge engagement is comparatively large and is detected only at the start and end of the measurement, a sliding mean is obtained which eliminates sharp signal contributions at the beginning and end of the strip which may distort the results obtained.

We have found that it is possible in this manner to provide a highly precise measurement of the tension distribution function across the width of the strip without problematical contributions at the edges which might otherwise result from a precipitous drop in a measured value or partial tension measurement at the starting and ending of the measurement. This has been shown diagrammatically by the vectors for the tension distribution in FIG. 1a.

The measurement roll 2 can be provided with a coating of tungsten carbide or with a hard chromium layer to minimize the wear and can have a cylindrical configuration although this is not compulsory. The measurement roller 2 can also have a coolant system or other temperature control arrangement for eliminating the temperature effects on the planarity measurements. A circulation of a coolant through the measuring roller can also eliminate temperature distortions at the force measurement cells d. This is especially advantageous when the measuring device is incorporated in a hot rolling line or the like.

Within the framework of the invention is an embodiment, previously mentioned and illustrated in FIG. 2 wherein pins bearing on force sensors are provided to engage the strip instead of the measuring beam 4. These pins have gaps between them and are sealed relative to the surface of the measuring roller by O-rings, plastic sensors or like sealing members which preclude the penetration of dirt into any clearance around the pin.

The measurement roller 2 can have one or more temperature sensors which not only enable the temperature of the strip 1 to be determined and thus a temperature profile for the strip to be measured but also enable control of the coolant demand for the measuring roller 2, i.e. the flow of coolant which will maintain a fixed temperature of the measuring roller and thus reduce the temperature effects during measurement to a minimum.

Figure 10A:
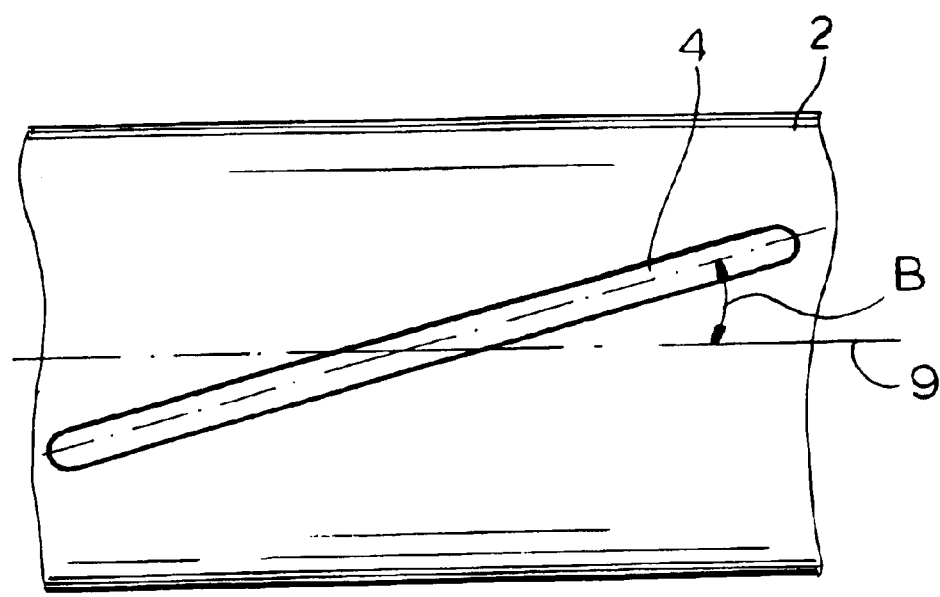
FIG. 10a is a detail of a measurement roller with an integrated measurement beam in vertical projection.
Figure 10B:
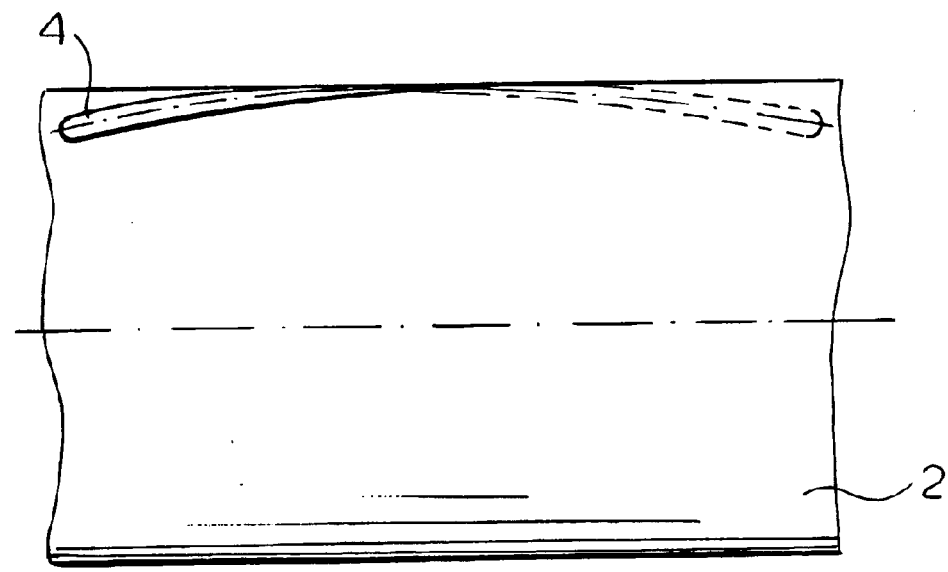
Figure 11:
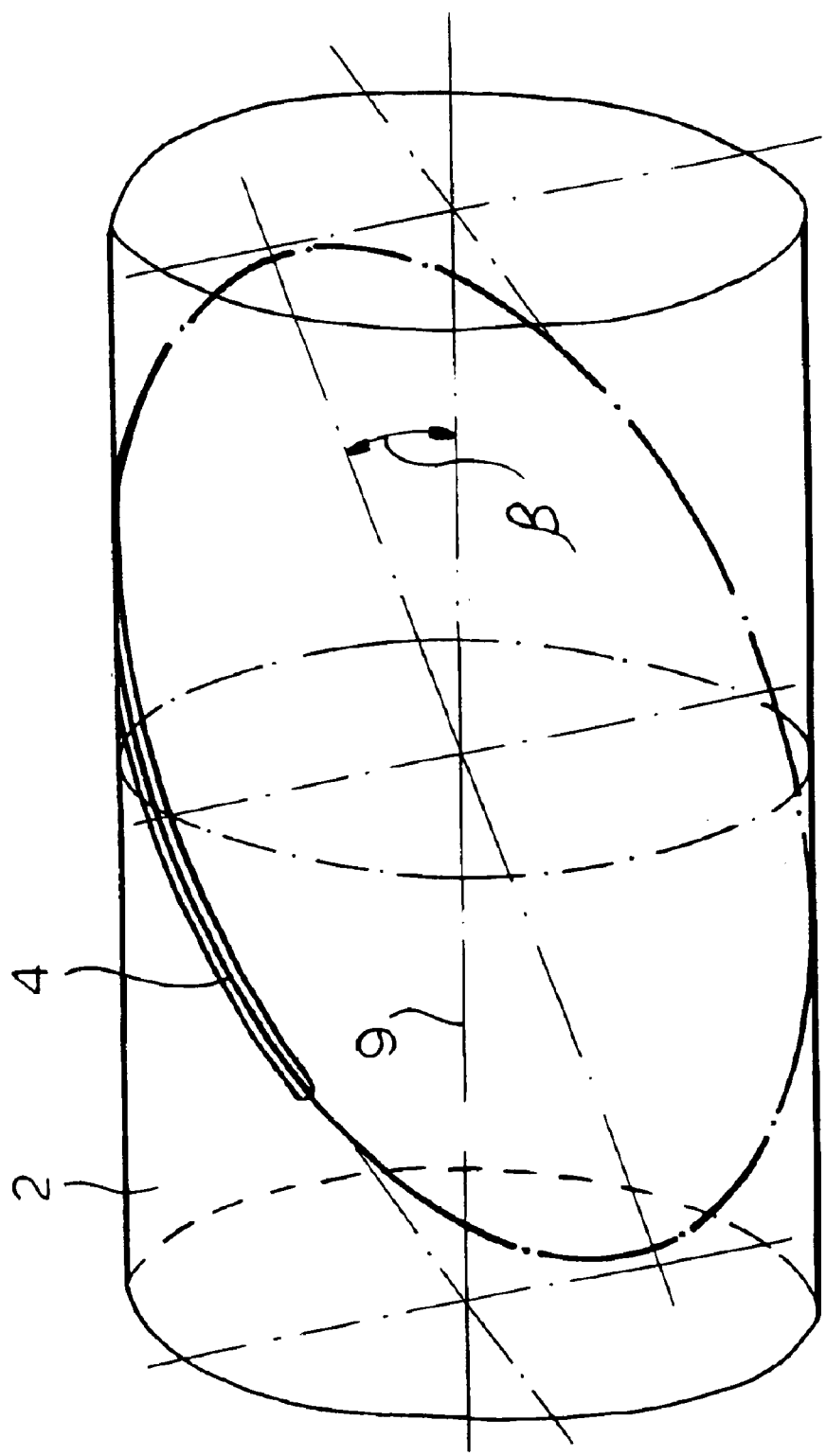
FIG. 11 is a perspective view of the measurement roller and the measurement beam of FIG. 10b.

FIGS. 10a, 10b and 11 show that the measuring beam 4 in vertical projection can have a predetermined angle of inclination β to the longitudinal axis 9 of the measuring roller 2. The measuring beam 4 lies generally along an ellipsoidal arc. As a consequence, not only can the tension force Fx and the tension distribution function $\sigma_x(y)$ be obtained in the longitudinal direction, i.e. the x direction but it is also possible to measure as an alternative or an addition, tension forces in the y direction.

FIG. 12 shows, as previously indicated, a measuring beam 4 which is received within a corresponding recess in the measuring roller and at its end can be provided with stems 5a which bear on respective load cells 5 connected by electrical conductors 5b to slip rings and wipers from which the measured values are delivered to the computer. The slip rings for the measuring roller have not been illustrated in the drawing.

We claim:

1. A method of measuring planarity of strip passing through a strip-rolling line or a strip-processing line, comprising the steps of:
   (a) measuring tension forces ($F_x$) acting upon the strip at least sectionwise over a width of the strip;
   (b) summing the measured tension forces ($F_x$) to form a force-summation function (F(y)) across the strip width; and
   (c) deriving a tension distribution function ($\sigma_x(y)$) from said force-summation function (F(y)), the tension forces ($F_x$) acting upon the strip being measured by at least one sensor over the width of the strip from one strip edge to an opposite strip edge in successive time intervals and the corresponding measurements along a respective measurement line or covering a respective measurement area of the strip are summed to form said summation function.

2. A method of measuring planarity of strip passing through a strip-rolling line or a strip-processing line, comprising the steps of:
   (a) measuring tension forces ($F_x$) acting upon the strip at least sectionwise over a width of the strip;
   (b) summing the measured tension forces ($F_x$) to form a force-summation function (F(y)) across the strip width; and
   (c) deriving a tension distribution function ($\sigma_x(y)$) from said force-summation function (F(y)), the tension forces ($F_x$) acting upon the strip being measured by at least one sensor over the width of the strip by passing the strip around a roller over a looping angle (α) and scanning the strip with said sensor between a starting position along one edge of said strip and an ending position along an opposite edge of said strip over a measurement angle on said roller within said looping angle (α).

3. A method of measuring planarity of strip passing through a strip-rolling line or a strip-processing line, comprising the steps of:
   (a) measuring tension forces ($F_x$) acting upon the strip at least sectionwise over a width of the strip;
   (b) summing the measured tension forces ($F_x$) to form a force-summation function (F(y)) across the strip-widths; and
   (c) deriving a tension distribution function ($\sigma_x(y)$) from said force-summation function (F(y)), sliding mean values of respective tension force measurements ($F_x$) being made across the strip width and the tension distribution function ($\sigma_x(y)$) being derived from the sliding mean values of respective tension force measurements ($F_x$).

4. A device for measuring planarity of strip passing through a strip-rolling line or a strip-processing line, comprising:
   an elongated sensor unit having at least one sensor for measuring tension forces ($F_x$) acting upon the strip at least sectionwise over a width of the strip, said sensor unit being oriented at an inclination to a direction of travel of the strip; and
   a computer unit connected to said sensor unit for summing the measured tension forces ($F_x$) to form a force-summation function (F(y)) across the strip width and deriving a tension distribution function ($\sigma_x(y)$) from said force-summation function (F(y))
   at least one measurement roller around which said strip is at least partially looped to form a looping angle (α) of the strip on said roller, said elongated sensor unit being a measurement beam integrated in said roller.

5. The device defined in claim 4 wherein said strip is scanned with said measurement beam between a starting position along one edge of said strip and an ending position along an opposite edge of said strip over a measurement angle on said roller within said looping angle (α).

6. The device defined in claim 5 wherein the measurement roller is provided with a plurality of measurement beams angularly spaced from one another for effecting a plurality of tension force measurements per revolution of said measurement roller.

7. The device defined in claim 4 wherein a plurality of measurement beams are provided along a length of said roller for measuring tension in respective longitudinal regions of said strip.

8. The device defined in claim 4 wherein said measurement beam in a vertical projection lies at a predetermined angle of inclination (β) to a main axis of the measurement roller.

9. A device for measuring planarity of strip passing through a strip-rolling line or a strip-processing line, comprising:

an elongated sensor unit having at least one sensor for measuring tension forces ($F_x$) acting upon the strip at least sectionwise over a width of the strip, said sensor unit being oriented at an inclination to a direction of travel of the strip; and a computer unit connected to said sensor unit for summing the measured tension forces ($F_x$) to form a force-summation function ($F(y)$) across the strip width and deriving a tension distribution function ($\sigma_x(y)$) from said force-summation function ($F(y)$) at least one measurement roller around which said strip is at least partially looped and provided with sensors of said sensor unit, said measurement roller being formed from individual roll segments which can be set at an inclination.

10. A measuring roller for measuring planarity of metal strip at least partly looped around said measuring roller in a strip processing or strip rolling line, comprising at least one linearly or helically extending measuring beam integrated in said measuring roller over the length thereof and having leading and trailing portions of said beam engaged by said strip within a looped region of the beam and subjected to forces applied to said beam by the strip, and force-measuring devices at ends of said measuring beam.

* * * * *